(12) United States Patent
Davey et al.

(10) Patent No.: US 7,674,932 B2
(45) Date of Patent: Mar. 9, 2010

(54) METHOD FOR THE PRODUCTION OF UREA FROM NATURAL GAS

(75) Inventors: William Davey, Frankfurt am Main (DE); Thomas Wurzei, Oberursel/Ts (DE)

(73) Assignee: Lurgi AG, Frankfurt am Main (DE)

( * ) Notice: Subject to any disclaimer, the term of this patent is extended or adjusted under 35 U.S.C. 154(b) by 54 days.

(21) Appl. No.: 11/665,278

(22) PCT Filed: Aug. 18, 2005

(86) PCT No.: PCT/EP2005/008936

§ 371 (c)(1),
(2), (4) Date: Nov. 29, 2007

(87) PCT Pub. No.: WO2006/039960

PCT Pub. Date: Apr. 20, 2006

(65) Prior Publication Data

US 2008/0207948 A1    Aug. 28, 2008

(30) Foreign Application Priority Data

Oct. 12, 2004    (DE) .................. 10 2004 049 774

(51) Int. Cl.
*C07C 273/02* (2006.01)
*C07C 237/04* (2006.01)

(52) U.S. Cl. ................. 564/63; 564/69; 564/70; 564/72

(58) Field of Classification Search ............ 564/63, 564/67, 69, 72
See application file for complete search history.

(56) References Cited

U.S. PATENT DOCUMENTS

| 4,409,196 A | 10/1983 | Skinner et al. ............. 423/359 |
| 6,231,827 B1 | 5/2001 | Pagani et al. ............... 423/359 |
| 6,448,441 B1 | 9/2002 | Wing-Chiu et al. .......... 564/67 |
| 2004/0028595 A1 | 2/2004 | Davey et al. |

*Primary Examiner*—Peter G O'Sullivan
(74) *Attorney, Agent, or Firm*—Jonathan Myers; Andrew Wilford

(57) ABSTRACT

Disclosed is a method for the production of urea from natural gas, wherein a) natural gas undergoes partial oxidation or autothermal reformation with a gas containing oxygen in a first step and the raw synthesis gas thus arising, consisting essentially of carbon monoxide, carbon dioxide, methane and hydrogen, can be transformed by catalytic conversion of CO and $H_2O$ to form $CO_2$ and $H_2$, whereupon carbon monoxide and methane are removed in a multistep gas cleaning process and the hydrogen is converted into ammonia upon addition of nitrogen, and subsequently, b) the ammonia is recombined with the previously separated carbon dioxide in a second step and the ammonia is thus fully converted into urea.

3 Claims, 2 Drawing Sheets

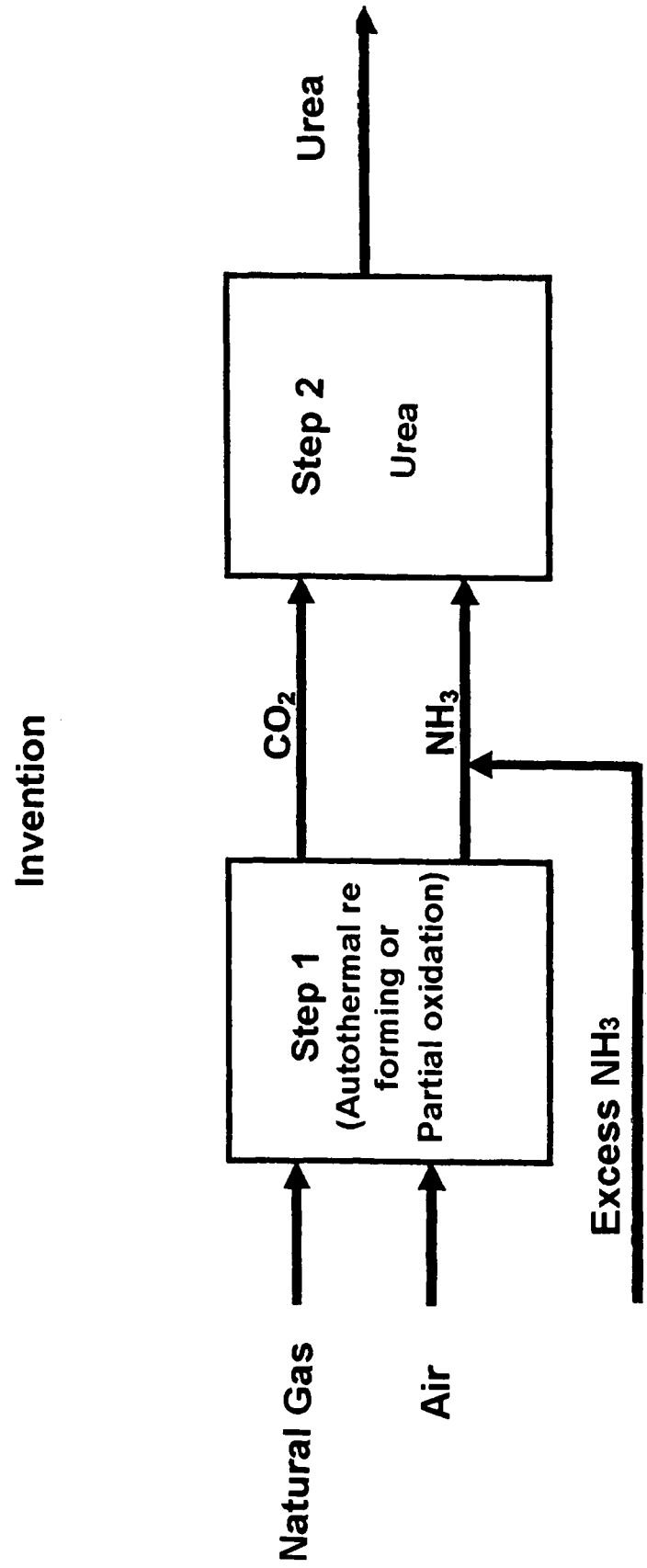

METHOD FOR THE PRODUCTION OF UREA FROM NATURAL GAS

CROSS REFERENCE TO RELATED APPLICATIONS

Figure 1:
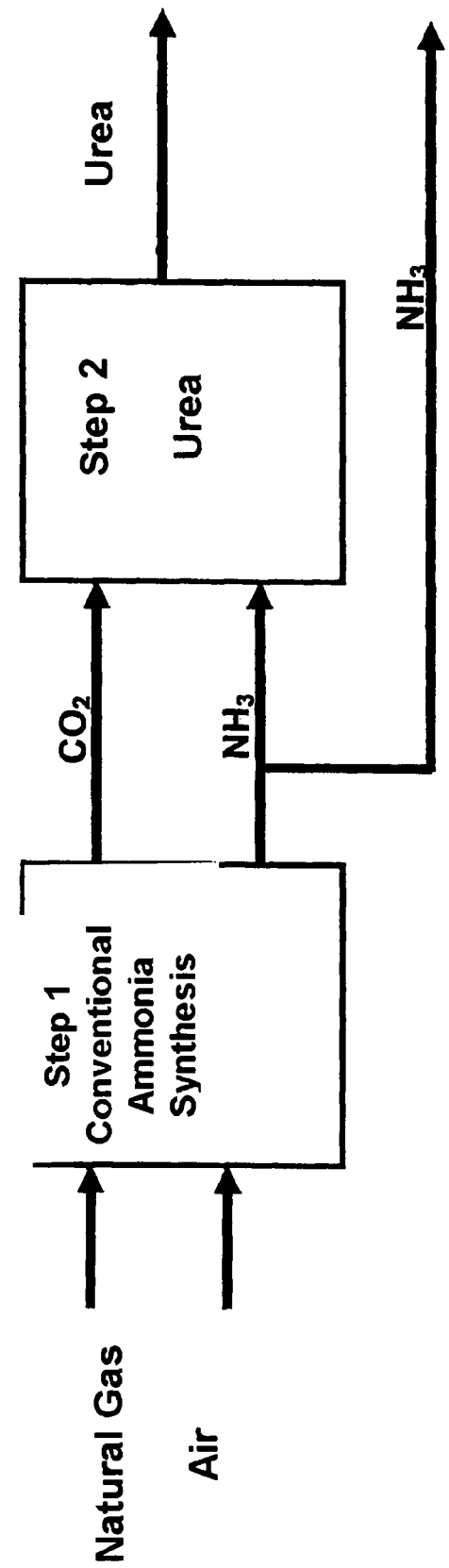

This application is the US national phase of PCT application PCT/EP2005/008936, filed 18 Aug. 2005, published 20 Apr. 2006 as WO 2006/039960, and claiming the priority of German patent application 102004049774.5 itself filed 12 Oct. 2004.

The invention relates to a two-step method for producing urea from natural gas, where in a first method step ammonia and carbon dioxide are produced, and in a second method step they are reacted with one another to form urea. In particular, the invention relates to producing stoichiometric and superstoichiometric quantities of urea from natural gas.

It is known that it is possible to produce urea from natural gas in a two-step method.

In a first step, nitrogen is bound as ammonia, and at the same time carbon dioxide is produced from the natural gas, while in a second method step the ammonia and the carbon dioxide are converted to urea. It is also known that the quantity of urea that can be produced using this method is limited by the quantity of carbon dioxide that can be obtained in the first method step.

Normally, in the first method step, that is the ammonia synthesis, a synthesis gas is produced from natural gas, and an oxygen-containing gas, e.g. air, in a steam reformer, and then in a further method step ("secondary reformer") the oxidation of the carbohydrates contained in the natural gas is largely concluded. This method leads to a synthesis gas, whose carbon dioxide content is about 10% less than is stoichiometrically required for converting the simultaneously resulting ammonia to urea. Therefore all such methods for producing urea involve the problem of how to use the excess ammonia.

A new method has now been found in which the quantity of the carbon dioxide produced using partial oxidation of the natural gas is equal to or greater than the stoichiometric quantity that is required for converting the ammonia to urea. With this method it is therefore possible not only to convert all of the resultant ammonia to urea, but it is also even possible to produce large enough quantities of carbon dioxide to convert additional ammonia that has been added from an external ammonia source, which means in accordance with the invention a substantially higher quantity of urea can be produced than with conventional methods.

The subject of the invention is therefore a method for producing urea from natural gas in which:

a) in a first method step natural gas and an oxygen-containing gas are subjected to partial oxidation or to autothermal reformation and the resultant raw synthesis gas, largely comprising carbon monoxide, carbon dioxide, methane, and hydrogen, is converted from CO and $H_2O$ to $CO_2$ and $H_2$ using catalytic conversion, then in a multistep gas purification carbon dioxide, carbon monoxide, and methane are removed from the synthesis gas and, after the addition of nitrogen, the remaining hydrogen is catalytically converted to ammonia, and then b) in a second method step the ammonia is recombined with the previously separated carbon dioxide and all of the ammonia is converted.

In particular, however, it is possible in the second method step to also add $NH_3$ from an external ammonia source such that all of the excess carbon dioxide formed in the first step can be converted to urea.

The inventive method for the catalytic production of ammonia from a nitrogen/hydrogen mixture, used in the first method step, was described in German patent 100 55 818 [US 2004/0028595]. In it, natural gas together with an oxygen-rich gas are conducted into an autothermal reformer where a raw synthesis gas is produced at temperatures ranging from 900 to 1200° C., a pressure of 40 to 100 bar, and in the presence of a catalyst. This synthesis gas, calculated dry, has an $H_2$ content of 55 to 75 percent by volume, a CO content of 15 to 30 percent by volume, a $CO_2$ content of 5 to 30 percent by volume, and a $H_2$:CO volume ratio of 1.6 to 4. The raw synthesis gas is then drawn out of the autothermal reformer, cooled, conducted through a catalytic conversion for converting the CO to $H_2$, and a converted synthesis gas with a $H_2$ content, calculated dry, of no less than 55 percent by volume and a CO content of no more than 8 percent by volume is drawn off. The converted synthesis gas is then subjected to a multistep gas purification for removing $CO_2$, CO, and $CH_4$, and a nitrogen/hydrogen mixture is produced that is catalytically converted to ammonia.

In general the natural gas used as the starting material largely comprises methane. In this case, the quantity of carbon dioxide obtained therefrom is stoichiometrically adequate for converting to urea ammonia formed in the first step of the inventive method. In this case, then, there will be no excess of ammonia. However, if the starting material also contains larger quantities of higher hydrocarbons, which is frequently the case, then the quantity of the carbon dioxide formed in the first step of the inventive method exceeds the stoichiometrically required quantity by up to 10%. This means that additional ammonia can be added to the reaction, either from an adjacent system or from purchased supplies, which then causes the quantity of the inventively formed urea to exceed that of a conventional system for ammonia production by up to 20%. This demonstrates the significantly improved efficiency of the inventive method for producing urea compared to all previously known methods for producing urea from natural gas.

For the first step of the inventive method it is important that a system for steam reforming is not used when producing the raw synthesis gas. Instead, in accordance with the invention an autothermal reformer is used that works at relatively high pressures that range from 30 to 100 bar, and primarily between 40 and 80 bar. Downstream of the autothermal reformer this high pressure can be maintained approximately so that the synthesis gas only has to be compressed slightly prior to beginning the ammonia synthesis. This is significantly more cost effective compared to conventional methods with steam reforming, in which only relatively low pressures are permitted. Compared to steam reforming, the autothermal reformer has the additional advantage that it provides a gas with an adequate $H_2/CO_2$ ratio, so that, as already mentioned in the foregoing, after the conversion with the $CO_2$ occurring in the gas purification, all of the $NH_3$ produced can be converted to urea.

Thus, in the inventive method, in the first method step a catalytic conversion is performed in which the carbon monoxide and $H_2O$ are converted to $CO_2$ and $H_2$. This is then followed by a multistage gas purification for removing carbon dioxide, carbon monoxide, and methane. A washing process in which e.g. methanol is used at temperatures ranging from −20 to −70° C. is particularly advantageous. Only relatively little energy, including compression energy, is used for this.

It is useful when the oxygen-rich gas added to the autothermal reformer has an oxygen content of no less than 70 percent by volume and in general even no less than 90 percent by volume. In this manner the content of impurities in the synthesis gas is reduced and the washing step can be reduced. The hydrogen to $CO_2$ volume ratio for the synthesis gas leaving the conversion is preferably 2 to 3 (dry calculation).

The block diagrams attached as FIG. 1 and FIG. 2 demonstrate the advantages of the inventive method compared to a method in accordance with the prior art. FIG. 1 shows the prior art. In accordance with this method, a gas mixture made of ammonia and carbon dioxide is produced from natural gas and air in the first method step, but it contains 10% less carbon dioxide than is required for stoichiometric conversion to urea. Excess ammonia must therefore be removed from the system. Steam reforming and subsequent second reforming characterize the conventional method.

In contrast, FIG. 2 depicts the inventive method in which partial oxidation or autothermal reformation is used, as is described in German patent application 100 55 818. In this method ammonia added from outside can be used to bond the excess carbon dioxide formed. This causes substantial quantities of additional urea to be formed.

Special advantages of the inventive method result when the inventive method is combined e.g. with an adjacent system for methanol synthesis from natural gas. Such a system produces plenty of excess carbon dioxide that can be added to the inventive method and with ammonia from an external source contributes to further increasing the yield of urea.

The invention claimed is:

1. A method for producing urea from natural gas wherein
   a) in a first method step natural gas and a an oxygen-containing gas is subjected to partial oxidation or to autothermal reformation and the resultant raw synthesis gas, largely comprising carbon monoxide, carbon dioxide, methane, and hydrogen, is converted from CO and $H_2O$ to $CO_2$ and $H_2$ using catalytic conversion, then in a multistep gas purification carbon dioxide, carbon monoxide, and methane are removed and, after the addition of nitrogen, the hydrogen is catalytically converted to ammonia, and then
   b) in a second method step the ammonia is recombined with the previously separated carbon dioxide and $NH_3$ from an external ammonia source is added such that all of the carbon dioxide is converted to urea.

2. The method in accordance with claim 1 wherein the oxygen-containing gas used for the partial oxidation has an oxygen content of no less than 70 percent by volume.

3. The method in accordance with claim 1 wherein the synthesis gas leaving the conversion has a hydrogen:$CO_2$ volume ratio of 2 to 3 (dry calculation).

* * * * *

UNITED STATES PATENT AND TRADEMARK OFFICE
CERTIFICATE OF CORRECTION

| | | |
|---|---|---|
| PATENT NO. | : 7,674,932 B2 | Page 1 of 1 |
| APPLICATION NO. | : 11/665278 | |
| DATED | : March 9, 2010 | |
| INVENTOR(S) | : William Davey et al. | |

It is certified that error appears in the above-identified patent and that said Letters Patent is hereby corrected as shown below:

On the Title page, Item (75) the correct spelling of the second inventor's name is:

-- Thomas Wurzel --

Signed and Sealed this

Eleventh Day of May, 2010

David J. Kappos
*Director of the United States Patent and Trademark Office*